United States Patent
Tunheim et al.

(10) Patent No.: US 9,103,716 B2
(45) Date of Patent: Aug. 11, 2015

(54) HANDHELD CHARACTERISTIC ANALYZER AND METHODS OF USING THE SAME

(75) Inventors: Ola Tunheim, Bryne (NO); Marshall E. Webster, Houston, TX (US); Alexis Wachtel, II, Houston, TX (US); Robert P. Freese, Pittsboro, NC (US); James R. MacLennan, Aberdeen (GB)

(73) Assignee: Halliburton Energy Services, Inc., Houston, TX (US)

( * ) Notice: Subject to any disclaimer, the term of this patent is extended or adjusted under 35 U.S.C. 154(b) by 414 days.

(21) Appl. No.: 13/600,288

(22) Filed: Aug. 31, 2012

(65) Prior Publication Data
US 2014/0061513 A1 Mar. 6, 2014

(51) Int. Cl.
| | |
|---|---|
| G01N 21/00 | (2006.01) |
| G01J 3/28 | (2006.01) |
| G01J 3/02 | (2006.01) |
| G01N 21/55 | (2014.01) |
| G01N 21/94 | (2006.01) |
| G01J 3/32 | (2006.01) |

(Continued)

(52) U.S. Cl.
CPC ............. *G01J 3/0264* (2013.01); *G01J 3/0272* (2013.01); *G01J 3/32* (2013.01); *G01N 21/55* (2013.01); *G01N 21/94* (2013.01); *G01J 2003/1213* (2013.01); *G01N 21/35* (2013.01); *G01N 21/359* (2013.01); *G01N 21/474* (2013.01); *G01N 21/645* (2013.01); *G01N 21/65* (2013.01); *G01N 2201/0221* (2013.01)

(58) Field of Classification Search
CPC .......................................................... G01J 3/02
USPC ................... 250/564; 356/326–330, 432–448
See application file for complete search history.

(56) References Cited

U.S. PATENT DOCUMENTS

| | | | |
|---|---|---|---|
| 6,198,531 B1 | 3/2001 | Myrick et al. | |
| 6,246,471 B1 * | 6/2001 | Jung et al. | 356/73 |

(Continued)

FOREIGN PATENT DOCUMENTS

| | | |
|---|---|---|
| EP | 1969326 | 9/2008 |
| EP | 2140238 | 5/2013 |

(Continued)

OTHER PUBLICATIONS

International Search Report and Written Opinion for PCT/US2013/056410 dated Nov. 29, 2013.

(Continued)

*Primary Examiner* — Renee D Chavez
(74) *Attorney, Agent, or Firm* — McDermott Will & Emery LLP; Anthony Iannitelli

(57) ABSTRACT

Disclosed is a portable handheld characteristic analyzer used to analyze chemical compositions in or near real-time. The analyzer may include a portable housing, at least one optical computing device arranged within the portable housing for monitoring a sample, the at least one optical computing device having at least one integrated computational element configured to optically interact with the sample and thereby generate optically interacted light, at least one detector arranged to receive the optically interacted light and generate an output signal corresponding to a characteristic of the sample, and a signal processor communicably coupled to the at least one detector for receiving the output signal, the signal processor being configured to determine the characteristic of the sample and provide a resulting output signal indicative of the characteristic of the sample.

19 Claims, 3 Drawing Sheets

(51) Int. Cl.
  *G01N 21/35*    (2014.01)
  *G01N 21/359*   (2014.01)
  *G01N 21/47*    (2006.01)
  *G01N 21/64*    (2006.01)
  *G01N 21/65*    (2006.01)
  *G01J 3/12*     (2006.01)

(56) References Cited

U.S. PATENT DOCUMENTS

| | | |
|---|---|---|
| 6,529,276 B1 | 3/2003 | Myrick |
| 7,123,844 B2 | 10/2006 | Myrick |
| 7,138,156 B1 | 11/2006 | Myrick et al. |
| 7,332,094 B2 | 2/2008 | Abney et al. |
| 7,472,748 B2 | 1/2009 | Gdanski et al. |
| 7,623,233 B2 | 11/2009 | Freese et al. |
| 7,697,141 B2 | 4/2010 | Jones et al. |
| 7,712,527 B2 | 5/2010 | Roddy |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,049,881 B2 | 11/2011 | Myrick et al. |
| 8,141,633 B2 | 3/2012 | Hampton et al. |
| 2005/0229698 A1 | 10/2005 | Beecroft et al. |
| 2007/0282647 A1 | 12/2007 | Freese et al. |
| 2008/0231849 A1 | 9/2008 | Myrick et al. |
| 2008/0276687 A1 | 11/2008 | Myrick et al. |
| 2009/0073433 A1 | 3/2009 | Myrick et al. |
| 2009/0097024 A1 | 4/2009 | Blackburn et al. |
| 2009/0140144 A1 | 6/2009 | Myrick et al. |
| 2009/0154288 A1 | 6/2009 | Heathman |
| 2009/0182693 A1 | 7/2009 | Fulton et al. |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0032572 A1 | 2/2010 | Shelley et al. |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0328669 A1 | 12/2010 | Myrick et al. |
| 2011/0048708 A1 | 3/2011 | Glasbergen et al. |
| 2011/0163046 A1 | 7/2011 | Neal et al. |
| 2011/0199610 A1 | 8/2011 | Myrick et al. |
| 2014/0061449 A1 | 3/2014 | Tunheim et al. |
| 2014/0080224 A1 | 3/2014 | Tunheim et al. |

FOREIGN PATENT DOCUMENTS

| | | |
|---|---|---|
| EP | 2087328 | 12/2014 |
| WO | 9952010 A2 | 10/1999 |
| WO | 2007064575 | 6/2007 |
| WO | 2006137902 A2 | 12/2007 |
| WO | 2006137902 A3 | 12/2007 |
| WO | 2008121715 A1 | 10/2008 |
| WO | 2014035767 A1 | 3/2014 |
| WO | 2014035823 A1 | 3/2014 |

OTHER PUBLICATIONS

Myrick et al., "Application of Multivariate Optical Computing to Near-Infrared Imaging," Proceedings of SPIE—International Society for Optical Engineering, vol. 4577, 2002, pp. 148-157, XP001152470.

International Search Report and Written Opinion for PCT/US2013/056013 dated Nov. 29, 2013.

Wilson et al., "Integrated Optical Computing for Portable, Real-Time SPR Analysis of Environmental Pollutants," Eurosensors, Prague, Czech Republic, 2002, XP009174277.

Van Der Meijde et al., "A Spectral-Geophysical Approach for Detecting Pipeline Leakage," International Journal of Applied Earth Observation Andgeoinformation, Elsevier, Amsterdam, NL, vol. 11, No. 1, 2009, XP025717096.

Halfang et al., "Remote Helicopter-Borne Laser Detector for Searching of Methane Leak of Gas Line," Prognostics and System Health Management Conference, 2011, IEEE, pp. 1-5, XP031998425.

Yamada et al., "Analysis of Black Powder in Natural Gas Pipeline," NACE, International Corrosion Conference Series, Houston, TX, 2011, pp. 585-598, XP009174408.

Myrick, et al. "Spectral Tolerance Determination for Multivariate Optical Element Design," Fresenuis' Journal of Analytical Chemistry, 369:2001; pp. 351-355.

Gdanski et al., "A New Model for Matching Fracturing Fluid Flowback Composition," 2007 SPE Hydraulic Fracturing Technology Conference held in College Station, Texas, SPE 106040.

Gdanski et al., "Using Lines-of-Solutions to Understand Fracture Conductivity and Fracture Cleanup," SPE Production and Operations Symposium held in Oklahoma City, OK, 2011, SPE 142096.

\* cited by examiner

HANDHELD CHARACTERISTIC ANALYZER AND METHODS OF USING THE SAME

BACKGROUND

The present invention relates to optical analysis systems and methods for analyzing chemical compositions and, in particular, to portable handheld characteristic analyzers used to analyze chemical compositions in or near real-time.

In the oil and gas industry, it can be important to precisely know the characteristics and chemical compositions of fluids and substances found in and about oil refineries or other hydrocarbon processing facilities. For example, there is an ever-increasing emphasis in reducing or otherwise preventing gaseous emissions and leaks from refineries and other processing facilities, given the environmental and health threats such emissions may pose. Knowing which chemical compositions are being emitted/leaked and the location and concentration of such emissions/leaks can prove advantageous in remedial efforts to reverse or stop the undesirable effects.

Detection and identification of chemical compositions include, inter alia, the use of surface acoustic wave detectors, ion mobility spectrometers, flame photometric detectors, and the like. In surface acoustic wave detectors, the target chemicals are absorbed or adsorbed onto a specific coating of a piezoelectric substrate, to thereby vary its mass. The mass change affects the resonance frequency of the piezoelectric substrate which is measured using an appropriate electronic circuitry. In ion mobility spectrometers, a gaseous sample is ionized in an ionization region within the spectrometer, e.g., using a radioactive source, and accelerated over a short distance to a detector. The gaseous sample is analyzed by measuring a characteristic time-of-flight of the negative and positive ions from the ionization region to the detector. In flame photometric detectors (FPDs) a gaseous sample is introduced to a hydrogen rich flame and electrons in the outer shell of atoms obtained from the target chemicals are excited to higher energy states. When an excited electron returns to its ground state, energy is emitted in the form of light by which the presence of target chemicals is confirmed. The wavelength of the emitted light depends on the target chemical, whereas its intensity depends on the chemical's concentration.

Portable detectors based on the above techniques are generally known. However, the above-noted techniques have limited sensitivity and selectivity in particular environments, such as industrial environments in which the detection and identification of chemical compositions are often performed under less than optimal conditions. Consequently, more accurate determinations of chemical compositions are usually conducted off-line using retrospective laboratory analyses, such as spectroscopic and/or wet chemical methods, which analyze an extracted sample of the chemical composition. Although off-line, retrospective analyses can be satisfactory in certain cases, they nonetheless do not allow real-time or near real-time analysis capabilities to be realized but instead often require hours to days to complete the analysis. During the lag time between collection and analysis, the characteristics of the extracted sample of the chemical composition oftentimes changes, thereby making the properties of the sample non-indicative of the true chemical composition or characteristic.

Reliable onsite, real-time detection of chemical compositions is of utmost importance in order to monitor how detected chemical compositions change over time, thereby serving as a quality control measure for processes in which fluids and other substances are used.

SUMMARY OF THE INVENTION

The present invention relates to optical analysis systems and methods for analyzing chemical compositions and, in particular, to portable handheld characteristic analyzers used to analyze chemical compositions in or near real-time.

In some aspects of the disclosure, a handheld characteristic analyzer is disclosed. The analyzer may include a portable housing, at least one optical computing device arranged within the portable housing for monitoring a sample, the at least one optical computing device having at least one integrated computational element configured to optically interact with the sample and thereby generate optically interacted light, at least one detector arranged to receive the optically interacted light and generate an output signal corresponding to a characteristic of the sample, and a signal processor communicably coupled to the at least one detector for receiving the output signal, the signal processor being configured to determine the characteristic of the sample and provide a resulting output signal indicative of the characteristic of the sample.

In other aspects of the disclosure, a method of determining a characteristic of a sample is disclosed. The method may include directing a handheld characteristic analyzer at the sample, the handheld characteristic analyzer having at least one integrated computational element arranged therein, activating the handheld characteristic analyzer, thereby optically interacting the at least one integrated computational element with the sample and generating optically interacted light, receiving the optically interacted light with at least one detector arranged within the handheld characteristic analyzer, generating an output signal corresponding to the characteristic of the sample with the at least one detector, receiving the output signal with a signal processor communicably coupled to the at least one detector, and determining the characteristic of the sample with the signal processor.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
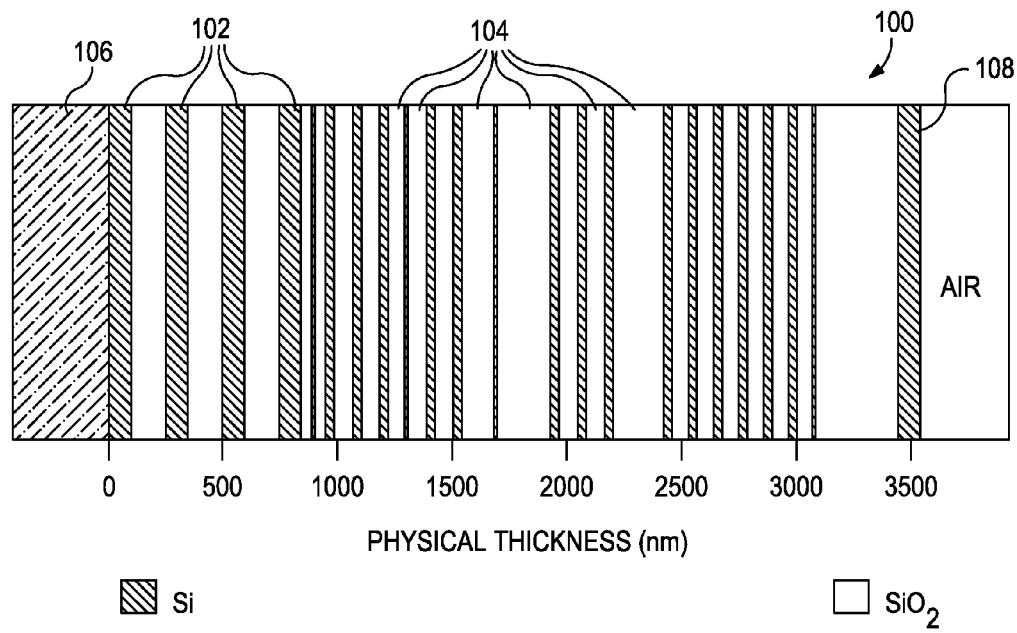
FIG. 1 illustrates an exemplary integrated computation element, according to one or more embodiments.

The present invention relates to optical analysis systems and methods for analyzing chemical compositions and, in particular, to portable handheld characteristic analyzers used to analyze chemical compositions in or near real-time.

The exemplary handheld characteristic analyzers described herein, and their various alternative embodiments, are able to employ various configurations of optical computing devices, also commonly referred to as "opticoanalytical devices," for the real-time or near real-time monitoring of chemical compositions found in fluids and other substances. In some cases, the exemplary handheld characteristic analyzers, as described herein, may be characterized as opticoanalytical devices. In operation, the exemplary handheld characteristic analyzer may be useful and otherwise advantageous in determining the presence and/or concentration of hazardous substances and/or contaminants that may exist in and around, for example, industrial equipment. For instance, the optical computing devices, which are described in more detail below, can advantageously provide real-time or near real-time monitoring of chemical compositions that cannot presently be achieved with either onsite analyses at a job site or via more detailed analyses that take place in a laboratory. Moreover, the portability of the exemplary handheld characteristic analyzers allow a user to selectively position the optical computing devices onsite at or near locations where a more direct detection of hazardous substances or contaminants can be had.

A significant and distinct advantage of these optical computing devices is that they can be configured to specifically detect and/or measure a particular component or characteristic of interest of a chemical composition, such as a hazardous substance or other contaminant present in the chemical composition, thereby allowing qualitative and/or quantitative analyses to occur without having to extract a sample of the chemical composition and undertake time-consuming analyses of the sample at an off-site laboratory. In some cases, the devices can monitor how the presence of a hazardous substance or contaminant in the chemical composition changes based on activity undertaken in the vicinity, such as remedial efforts focused on removing or otherwise containing the hazardous substance or contaminant.

With the ability to perform onsite, real-time or near real-time chemical composition analyses, the exemplary handheld characteristic analyzer, and its various alternative embodiments, may be able to provide a timely indication of either healthy or unhealthy environments surrounding various industrial equipment. In some cases, the handheld characteristic analyzer may be useful in the early detection of hydrocarbon leaks or the leakage of other environmentally hazardous substances or materials from oil and gas equipment. Detection of hydrocarbon leaks may prove advantageous in initiating preventative measures that stop the loss of valuable product into the surrounding environment. Moreover, once a hazardous substance or contaminant is detected in the surrounding environment, remedial efforts may be undertaken before environmental toxicity levels surpass a predetermined "healthy" limit, and thereby expose an operator to environmental and safety concerns, fines, unnecessary removal/remedial costs, and negative publicity.

Those skilled in the art will readily appreciate that the disclosed handheld characteristic analyzer, and its various alternative embodiments, may be suitable for use in the oil and gas industry since the described optical computing devices provide a cost-effective, rugged, and accurate means for monitoring industrial equipment in order to facilitate the efficient management of oil/gas production. It will be appreciated, however, that the disclosed handheld characteristic analyzer, and its various alternative embodiments, are equally applicable to other technology fields including, but not limited to, the food industry, the medicinal and drug industry, industrial applications, heavy machinery industries, mining industries, military fields, or any field where it may be advantageous to determine in real-time or near real-time the concentration or a characteristic of a chemical composition in a fluid or any other substance. For example, the exemplary handheld characteristic analyzer may be useful in the detection of contaminants in or properties of machinery lubricant fluid or grease, machinery hydraulic fluid, coolant fluid, and drinking water. In other applications, the exemplary handheld characteristic analyzer may be useful in the detection of water in gasoline or diesel fuel in machinery, or in providing a quick analysis of hydrocarbon recovered from an oil well.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water, such as seawater, fresh water, potable water, drinking water, or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquids and/or gases. Illustrative gases that can be considered fluids, according to the present embodiments, include, for example, air, nitrogen, carbon dioxide, argon, helium, methane, ethane, butane, and other hydrocarbon gases, combinations thereof and/or the like.

As used herein, the term "characteristic" refers to a chemical, mechanical, or physical property of a substance or material. A characteristic of a substance may include a quantitative value or a concentration of one or more chemical components present therein. Such chemical components may be referred to herein as "analytes." Illustrative characteristics of a substance that can be monitored with the optical computing devices disclosed herein can include, for example, chemical composition (e.g., identity and concentration in total or of individual components), impurity content, pH, viscosity, density, ionic strength, total dissolved solids, salt content, porosity, opacity, bacteria content, combinations thereof, and the like.

As used herein, the terms "hazardous substance" and "contaminant," and variations thereof, are used interchangeably herein and refer to a matter or material of interest to be evaluated using the handheld characteristic analyzer (i.e., with the optical computing devices arranged therein) described herein. In some embodiments, the hazardous substance is the characteristic of interest, as defined above, and may include any contaminating fluid or substance emitted from or otherwise associated with industrial equipment or machinery. In other embodiments, the hazardous substance may simply be an undesirable substance but not necessarily a substance that would be considered "hazardous," per se. For example, the hazardous substance may include non-hazardous analytes such as, but not limited to, nitrogen and helium, and could also include tracer and leak detection compounds or dyes used in testing operations.

In one or more embodiments, the hazardous substance may include chemicals such as BTEX compounds (i.e., benzene, toluene, ethylbenzene, and xylenes), volatile organic compounds (VOCs), naphthalene, styrene, sulfur compounds, hexane, hydrocarbons, liquefiable hydrocarbons, barium, boron, calcium, manganese, magnesium, magnesium alloys, phosphorus, potassium compounds, zinc, zinc alloys, copper, lead, tin, nickel, silver, molybdenum alloys, titanium alloys, combinations thereof, and any combination thereof. In other embodiments, the hazardous substance may include or otherwise refer to paraffins, waxes, asphaltenes, aromatics, saturates, foams, salts, bacteria, combinations thereof, and the like. In yet other embodiments, the hazardous substance may include compounds containing elements such as aluminum, aluminum alloys barium, calcium, manganese, magnesium, phosphorus, sulfur, iron, strontium, chlorine.

In other aspects, the hazardous substance may include any substance used in wellbore operations such as, but not limited to, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be used as well.

In embodiments where the hazardous substance is characterized as a contaminant, it may include, water, soot, glycol, oxidation products, wear debris, particulate contamination, combinations thereof, and the like. Various contaminants of, for example, drinking water may include aluminum, chloride, copper, fluoride, iron, manganese, sulfate, zinc, disinefectants, inorganic chemicals, acrylamide, bromate, chlorite, haloacetic acids (HAA5), total trihalomethanes (TTHMs), chloramines (as $Cl_2$), chlorine (as $Cl_2$), chlorine dioxide (as $ClO_2$), inorganic chemicals, antimony, antimony alloys, arsenic, asbestos (fiber>10 micrometers), barium, beryllium, cadmium, chromium (total), chromium alloys, copper, cyanide (as free cyanide), fluoride, lead, mercury (inorganic), nitrate (measured as nitrogen), nitrite (measured as nitrogen), selenium, thallium, acrylamide, alachlor, atrazine, benzene, benzo(a)pyrene (PAHs), carbofuran, carbon tetrachloride, chlordane, chlorobenzene, 2,4-D, dalapon, 1,2-dibromo-3-chloropropane (DBCP), o-dichlorobenzene, p-dichlorobenzene, 1,2-dichloroethane, 1,1-dichloroethylene, cis-1,2-dichloroethylene, trans-1,2-dichloroethylene, dichloromethane, 1,2-dichloropropane, di(2-ethylhexyl) adipate, di(2-ethylhexyl)phthalate, dinoseb, dioxin (2,3,7,8-TCDD), diquat, endothall, endrin, epichlorohydrin, ethylbenzene, ethylene dibromide, glyphosate, heptachlor, heptachlor epoxide, hexachlorobenzene, hexachlorocyclopentadiene, lindane, methoxychlor, oxamyl (vydate), polychlorinated biphenyls, pentachlorophenol, picloram, simazine, styrene, tetrachloroethylene, toluene, toxaphene, 2,4,5-TP (silvex), 1,2,4-trichlorobenzene, 1,1,1-trichloroethane, 1,1,2-trichloroethane, trichloroethylene, vinyl chloride, xylenes, silicon, combinations thereof, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance (e.g., a fluid or other material, such as a chemical composition) or a sample of the substance, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the substance being measured or monitored. The output of electromagnetic radiation from the processing element can be reflected electromagnetic radiation, transmitted electromagnetic radiation, and/or dispersed electromagnetic radiation. Whether the detector analyzes reflected or transmitted electromagnetic radiation may be dictated by the structural parameters of the optical computing device as well as other considerations known to those skilled in the art. In addition, emission and/or scattering of the substance, for example via fluorescence, luminescence, Raman scattering, and/or Raleigh scattering, can also be monitored by the optical computing devices. In some cases, the handheld characteristic analyzer itself, as generally described herein, may contain or otherwise be characterized as an optical computing device.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a fluid or any other substance.

As used herein, the term "sample," or variations thereof, refers to at least a portion of a substance or chemical composition of interest to be tested or otherwise evaluated using the handheld characteristic analyzer (and accompanying optical computing device(s)) described herein. The sample includes the characteristic of interest, as defined above, and may be any fluid, as defined herein, or otherwise any solid substance or material such as, but not limited to, rock formations, concrete, masonry (i.e., brick, tile, etc.), fiberglass, composites, metals, soil, weldments, plastics, other solid surfaces, and the like.

The exemplary handheld characteristic analyzer described herein, and its various alternative embodiments, will include or otherwise form part of at least one optical computing device for onsite, near or real-time monitoring of one or more chemical compositions, such as a hazardous substance or a contaminant present within a sample fluid or other substance. The optical computing device may include an electromagnetic radiation source, at least one processing element (e.g., integrated computational elements), and at least one detector arranged to receive optically interacted light from the at least one processing element. As disclosed below, however, in some embodiments the electromagnetic radiation source may be omitted from the optical computing device and instead the electromagnetic radiation may be derived from ambient light (e.g., the sun, natural fluorescence or luminescence, or other artificial light) or the chemical composition or substance itself. In some embodiments, the exemplary optical computing devices may be specifically configured for detecting, analyzing, and quantitatively measuring a particular characteristic or analyte of interest of the chemical composition. In other embodiments, the optical computing devices may be general purpose optical devices, with post-acquisition processing (e.g., through computer means) being used to specifically detect the characteristic of interest.

In some embodiments, suitable structural components for the exemplary optical computing devices are described in commonly owned U.S. Pat. Nos. 6,198,531; 6,529,276; 7,123,844; 7,834,999; 7,911,605; 7,920,258; and 8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample extraction and processing. In this regard, the optical computing devices can be specifically configured to detect and analyze particular characteristics and/or analytes of interest of a chemical composition, such as a hazardous substance or a contaminant present within a sample fluid or other substance. As a result, interfering signals are discriminated from those of interest in the sample fluid or other substance by appropriate configuration of the optical computing devices, such that the optical computing devices provide a rapid response regarding the characteristic(s) of interest based on the detected output. In some embodiments, the detected output can be converted into a voltage that is distinctive of the magnitude of the characteristic being monitored in the sample fluid or substance. The foregoing advantages and others make the exemplary handheld characteristic analyzer, and its accompanying optical computing devices, particularly well suited for onsite field use for any industrial application.

The optical computing device(s) arranged in the exemplary handheld characteristic analyzer can be configured to detect not only the composition and concentrations of a hazardous substance or contaminant in a sample fluid or substance, but they also can be configured to determine physical properties and other characteristics of the hazardous substance or contaminant as well, based on an analysis of the electromagnetic radiation received from the particular hazardous substance or contaminant. For example, the optical computing devices can be configured to determine the concentration of an analyte and correlate the determined concentration to a characteristic of a hazardous substance by using suitable processing means. As will be appreciated, the optical computing devices may be configured to detect as many hazardous substances or as many characteristics or analytes of the hazardous substance as desired in the sample fluid or substance. All that is required to accomplish the monitoring of multiple characteristics is the incorporation of suitable processing and detection means within the optical computing device for each hazardous substance or contaminant. In some embodiments, the properties of the hazardous substance can be a combination of the properties of the analytes detected therein (e.g., a linear, non-linear, logarithmic, and/or exponential combination). Accordingly, the more characteristics and analytes that are detected and analyzed using the optical computing devices, the more accurately the properties of the given hazardous substance will be determined.

The optical computing devices described herein utilize electromagnetic radiation to perform calculations, as opposed to the hardwired circuits of conventional electronic processors. When electromagnetic radiation interacts with a hazardous substance in a sample fluid or other substance, unique physical and chemical information about the hazardous substance may be encoded in the electromagnetic radiation that is reflected from, transmitted through, or radiated from the hazardous substance. This information is often referred to as the spectral "fingerprint" of the hazardous substance. The optical computing devices described herein are capable of extracting the information of the spectral fingerprint of multiple characteristics or analytes, and converting that information into a detectable output regarding the overall properties of the hazardous substance. That is, through suitable configurations of the optical computing devices, electromagnetic radiation associated with a characteristic or analyte of interest of a hazardous substance can be separated from electromagnetic radiation associated with all other components of the sample fluid or substance in order to estimate the properties of the hazardous substance in real-time or near real-time.

As stated above, the processing elements used in the exemplary optical computing devices described herein may be characterized as integrated computational elements (ICE). Each ICE is capable of distinguishing electromagnetic radiation related to a characteristic of interest corresponding to a hazardous substance from electromagnetic radiation related to other components of the hazardous substance or of the sample fluid or substance where the hazardous substance is found. Referring to FIG. 1, illustrated is an exemplary ICE 100 suitable for use in the optical computing devices used in the exemplary handheld characteristic analyzer described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest (e.g., a chemical composition of a hazardous substance or contaminant) using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the sample fluid or substance being monitored.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
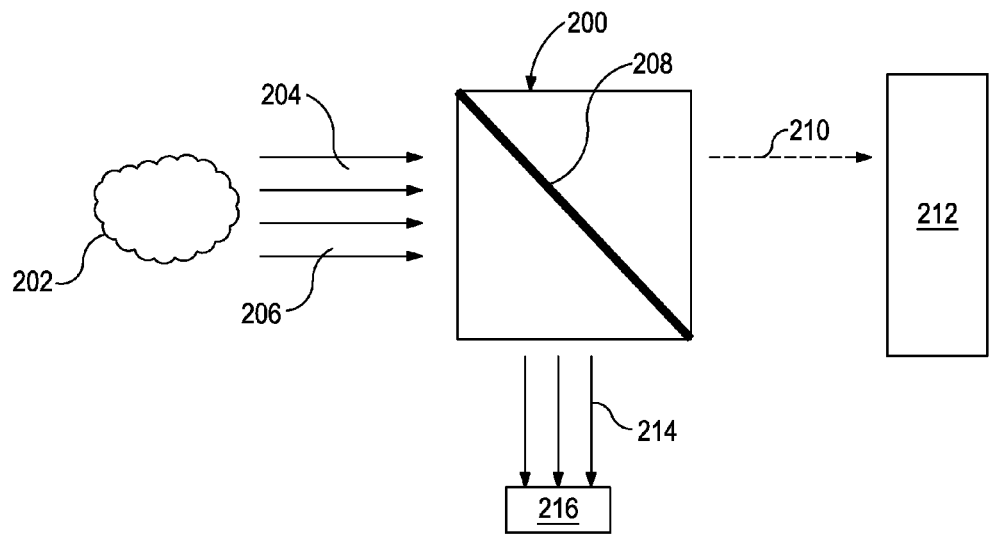
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, a sample 202 produces an output of electromagnetic radiation (e.g., sample-interacted light), some of which is electromagnetic radiation 204 corresponding to the characteristic of interest and some of which is background electromagnetic radiation 206 corresponding to other components or characteristics of the sample 202. In some embodiments, the sample 202 may be a fluid, but in other embodiments may be a solid substance, as defined herein. Moreover, in some embodiments, the sample 202 may include a hazardous substance or a contaminant and the characteristic of interest may correspond to the hazardous substance and/or contaminant.

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after the light source (if present), which provides the initial electromagnetic radiation. Various configurations and applications of spectral elements in optical computing devices may be found in commonly owned U.S. Pat. Nos. 6,198,531; 6,529,276; 7,123,844; 7,834,999; 7,911,605; 7,920,258; 8,049,881 and U.S. patent application Ser. No. 12/094,460 (U.S. Pat. App. Pub. No. 2009/0219538); U.S. patent application Ser. No. 12/094,465 (U.S. Pat. App. Pub. No. 2009/0219539); and U.S. patent application Ser. No. 13/456,467, incorporated herein by reference, as indicated above.

The beams of electromagnetic radiation 204, 206 impinge upon an exemplary ICE 208 arranged within the optical computing device 200. The ICE 208 may be similar to the ICE 100 of FIG. 1, and therefore will not be described again in detail. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to a characteristic of interest in the sample 202, may be conveyed to a detector 212 for analysis and quantification. In some embodiments, the detector 212 is configured to produce an output signal in the form of a voltage that corresponds to the particular characteristic of interest, such as a concentration of a hazardous substance found within the sample 202. In at least one embodiment, the signal produced by the detector 212 and the concentration of the characteristic of interest may be directly proportional. In other embodiments, the relationship may be a polynomial function, an exponential function, and/or a logarithmic function. The reflected optically interacted light 214, which may be related to characteristics of other components and chemical compositions of the sample 202, can be directed away from detector 212. In alternative configurations, the ICE 208 may be configured such that the reflected optically interacted light 214 can be related to the characteristic of interest, and the transmitted optically interacted light 210 can be related to other chemical compositions and/or components of the sample 202.

In some embodiments, a second detector 216 can be included in the optical computing device 200 and arranged to detect the reflected optically interacted light 214. In other embodiments, the second detector 216 may be arranged to detect the electromagnetic radiation 204, 206 derived from the sample 202 or electromagnetic radiation directed toward or before the sample 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to one or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to or otherwise being detected by the second detector 212.

The characteristic(s) of interest being analyzed using the optical computing device 200 can be further processed computationally to provide additional characterization information about the sample 202, or any hazardous substances or contaminants present therein. In some embodiments, the identification and concentration of each analyte of interest in the sample 202 can be used to predict certain physical characteristics of the sample 202. For example, the bulk characteristics of the sample 202 can be estimated by using a combination of the properties conferred to the sample 202 by each analyte.

In some embodiments, the concentration or magnitude of the characteristic of interest determined using the optical computing device 200 can be fed into an algorithm operating under computer control. The algorithm may be configured to make predictions on how the characteristics of the sample 202 would change if the concentrations of the characteristic of interest are changed relative to one another. In some embodiments, the algorithm can produce an output that is readable by an operator for consideration. For example, based on the output, the operator may want to undertake some remedial action to remedy, reduce, or otherwise prevent the future detection of a monitored hazardous substance or contaminant. In other embodiments, the algorithm can be programmed to take proactive process control by automatically initiating a remedial effort when a predetermined toxicity level of the hazardous substance is reported or otherwise detected.

The algorithm can be part of an artificial neural network configured to use the concentration of each characteristic of interest in order to evaluate the overall characteristic(s) of the sample 202 and thereby determine when a predetermined toxicity level has been reached or otherwise surpassed. Illustrative but non-limiting artificial neural networks are described in commonly owned U.S. patent application Ser. No. 11/986,763 (U.S. Patent App. Pub. No. 2009/0182693), which is incorporated herein by reference. It is to be recognized that an artificial neural network can be trained using samples of predetermined characteristics of interest, such as known hazardous substances and contaminants, having known concentrations, compositions, and/or properties, and thereby generating a virtual library. As the virtual library available to the artificial neural network becomes larger, the neural network can become more capable of accurately predicting the characteristic of interest corresponding to a sample fluid or other substance having any number of analytes present therein. Furthermore, with sufficient training, the artificial neural network can more accurately predict the characteristics of the sample fluid or substance, even in the presence of unknown hazardous substances or contaminants.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site but able to access the job site via wireless communication.

Figure 3A:
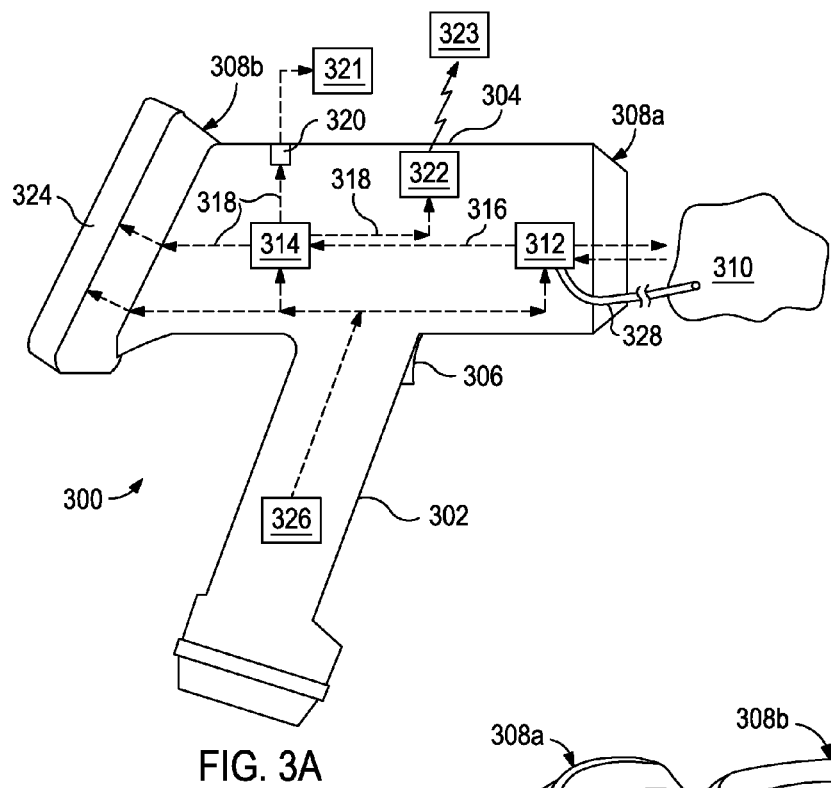
FIGS. 3A and 3B illustrate side and perspective views of an exemplary handheld characteristic analyzer, according to one or more embodiments.
Figure 3B:
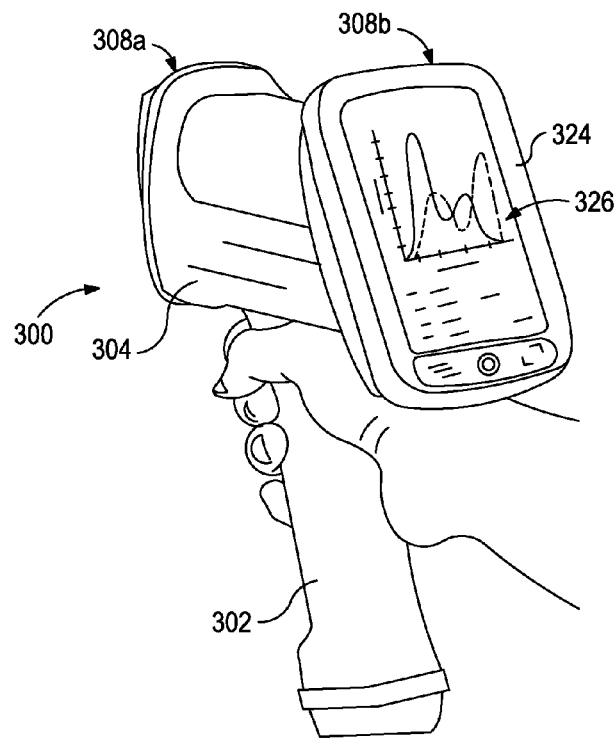

Referring now to FIGS. 3A and 3B, illustrated are side and perspective views, respectively, of an exemplary handheld characteristic analyzer 300, according to one or more embodiments. While a particular design of the handheld characteristic analyzer 300 is depicted and described herein, those skilled in the art will readily appreciate that various design modifications and alterations to the handheld characteristic analyzer 300 may be had. For example, while the handheld characteristic analyzer 300 is illustrated as being designed generally in the shape of a gun or the like, those skilled in the art will appreciate that other design shapes and configurations could also be used and nonetheless remain within the scope of the disclosure. In some embodiments, for instance, the analyzer 300 may simply be configured as a portable device that could be employed on-site for real-time or near real-time chemical and/or substance analysis.

As illustrated, in some embodiments, the handheld characteristic analyzer 300 may have a handle 302 for gripping or otherwise holding the handheld characteristic analyzer 302, and a housing 304 for encasing the various internal components of the analyzer 300. In other embodiments, the analyzer 300 may be gripped or otherwise manually held in varying other configurations, without departing from the scope of the disclosure. In some embodiments, the handle 302 forms part of the housing 304, but in other embodiments the handle 302 extends from the housing 304 as a separate component thereof. The handle 302 may define or otherwise provide a trigger mechanism 306 that may be manually engaged by a user when it is desired to initiate or otherwise activate the handheld characteristic analyzer 300 and thereby provide a measurement or reading. In some embodiments, the characteristic analyzer 300 may also be configured to capture a visual light image, similar to a digital camera, and the trigger mechanism 306 may further be configured to initiate the capture of the visual light image. Accordingly, activating the characteristic analyzer 300 may also refer to the capture, recording, and/or display of a visual light image.

The housing 304, or the analyzer 300 itself, may have a detection end 308a and an output end 308b. At the detection end 308a, the analyzer 300 may be configured to capture electromagnetic radiation provided from a sample 310 and thereby determine a characteristic of interest in the sample 310. The sample 310 may be similar to the sample 202 of FIG. 2 and, therefore, may include any fluid or solid substance as generally defined herein. In one or more embodiments, the sample 310 may include at least one hazardous substance or contaminant present therein, and the characteristic of interest as determined by the analyzer 300 may be indicative of a concentration of the hazardous substance or contaminant as measured within the sample 310.

In order to determine the characteristic of interest in the sample 310, the analyzer 300 may utilize an optical computing device 312 arranged therein and configured to optically interact with the sample 310. In some embodiments, the optical computing device 312 may be similar to the optical computing device 200 of FIG. 2. In at least one embodiment, however, the analyzer 300 itself may be characterized as the optical computing device with the various components of the optical computing device 312 arranged therein for proper functionality.

In operation, the detection end 308a of the analyzer 300 may be aimed at the sample 310 and the trigger mechanism 306 may subsequently be actuated to initiate a reading from the analyzer 300. Upon actuating the trigger mechanism 306, and as will be described in more detail below, the optical computing device 312 may be configured to receive and detect optically interacted radiation as derived from the sample 310. In at least one embodiment, the optical computing device 312 may be configured to provide an initial impulse of electromagnetic radiation to the sample 310 from an electromagnetic radiation source (not shown) in order to generate the optically interacted radiation. In other embodiments, however, ambient light, such as light from the sun or other artificial light, may provide sufficient electromagnetic radiation such that optically interacted light corresponding to the sample 310 is generated and detectable by the optical computing device 312.

The optical computing device 312 may be communicably coupled to a signal processor 314 also arranged within the housing 304 or otherwise forming part of the analyzer 300. In real-time or near real-time, the optical computing device 312 may be configured to generate an output signal 316 corresponding to the particular characteristic of interest as detected in the sample 310. The output signal 316 may be conveyed to the signal processor 314 which converts the output signal 316 into a resulting output signal 318 indicative of the characteristic of interest. The signal processor 314 may be communicably coupled to one or more communication interfaces and otherwise configured to convey the resulting output signal 318 thereto. For example, one communication interface may be a communication port 320 (compatible with Ethernet, USB, etc.) defined or otherwise provided on the analyzer 300 which allows the analyzer 300 to be coupled to an external processing device 321, such as a computer, a hard drive, a handheld computer, a personal digital assistant (PDA), or other wireless transmission device. Once coupled to the external processing device 321, the signal processor 314 may be able to download data (e.g., data related to the characteristic of interest) thereto, for example, from an on-board memory forming part of the signal processor 314.

In other embodiments, the communication interface may be a wireless transmitter or link 322 arranged within the housing 304. The signal processor 314 may be communicably coupled to the wireless link 322 and configured to convey the resulting output signal 318 thereto, which may operate in accordance with any known wireless technology (e.g., Bluetooth, Wi-Fi, etc.) and therefore be configured to wirelessly telecommunicate with any remote wireless device 323, such as, but not limited to, radios, cellular telephones, PDAs, wireless networks, satellite telecommunications, and the like.

In yet other embodiments, the communication interface may be a graphical user interface (GUI) 324 arranged on or otherwise forming part of the housing 304 of the analyzer 300 at the output end 308b. The signal processor 314 may be communicably coupled to the GUI 324 and configured to convey the resulting output signal 318 thereto. The GUI 324 may be configured to provide one or more visual representations of the characteristic of interest as detected in the sample 310. In some embodiments, the GUI 324 may be a capacitive touch screen, liquid crystal display, or other type of known electronic visual display. The GUI 324 may include a physical input keyboard (not shown), or the like, thereby enabling the user to interactively communicate with the signal processor 314 and the analyzer 300.

As illustrated in FIG. 3B, the GUI 324 may be able to provide the user with an imaging screen depicting, for example, an optical spectra 326 of the detected characteristic of interest. Embodiments contemplated herein, however, further include the GUI 324 as being able to interactively scroll between an imaging screen, to an averaging screen, to a compositional or characteristic screen, etc. The GUI 324 may be configured to display graphs showing changing concentrations of various chemicals calculated from spectra readings. In some embodiments, the GUI 324 may be configured to display concentration levels of several substances or chemical compounds simultaneously, and/or the level of match to a compound or characteristic. This may prove especially useful or advantageous in determining oil grades, types, and/or classes, where each grade, type, and/or class has mainly the same chemical constituents but at different levels or concentrations.

In some embodiments, the GUI 324 may indicate that concentration levels of certain chemicals have reached or otherwise are within a safe operational limit. The GUI 324 may be color-coded, where predetermined colors (e.g., green, yellow, red) may correspond to concentrations/characteristics that are considered neutral, warning, and unsafe, respectively. The safe operational limit may be, for example, predefined by a user on a chemical by chemical basis (or on a characteristic by characteristic basis) when initially configuring the analyzer 300 for operation. Additionally, the GUI 324 may be configured to provide or otherwise display trend data relating to particular chemical concentrations. Such trend data may be time and date stamped for user convenience. Accordingly, in at least one embodiment, the GUI 324 may be configured to present trend data over time, either from the present sample 310, or trend data derived from historic samples during a larger or shorter time span.

In some embodiments, the imaging screen of the GUI 324 may be configured for or otherwise capable of image overlay functionality. Briefly, the GUI 324 may be capable of combining two or more graphical images and producing a combined image that indicates or enhances particular features of one of the images. For example, the analyzer 300 may be capable of capturing a visual light image of an object (e.g., similar to a digital camera) where it is desired to monitor or otherwise detect a sample 310 of interest. The GUI 324 may be programmed with an image overlay mode that may be configured to overlay the captured visual light image with chemical composition or concentration information, as derived through the optical computing device 312. As can be appreciated, such functionality may prove advantageous in uses such as, but not limited to, leak detection, spill monitoring, contamination inspection, etc.

In some embodiments, the analyzer 300 may include one or more fiber optic probes 328 communicably coupled to or otherwise forming part of the optical computing device 312. In some embodiments, the fiber optic probes 328 may be configured to convey electromagnetic radiation to the sample 310 for the purpose of determining the particular characteristic of interest. In other embodiments, the fiber optic probes 328 may be configured to convey optically interacted radiation from the sample 310 to the optical computing device 312. In yet other embodiments, the fiber optic probes may be configured to both convey electromagnetic radiation to the sample 310 and convey optically interacted radiation from the sample 310 to the optical computing device 312.

The fiber optic probes 328 may be releasably or otherwise temporarily attached to the analyzer 300 at the detection end 308a. The fiber optic probes 328 may be any type of optical light pipe known to those skilled in the art including, but not limited to, infrared fiber optic probes, mid-infrared fiber optic probes, reflectance probes, fluorescence probes, side-looking probes, combinations thereof, and the like. Additional details on types and configurations of suitable fiber optic probes 328 can be found in the articles "Fiber-optic Probes for Mid-infrared Spectrometry," by Peter J. Melling and Mary Thomson, *Handbook of Vibrational Spectroscopy*, 2002, and "Fiber Optic Probes for Biomedical Optical Spectroscopy," by Urs Utzinger and Rebecca R. Richards-Kortum, *Journal of Biomedical Optics* 8(1), pp 121-147 (January 2003), each of which is hereby incorporated by reference in their entireties.

The fiber optic probes 328 may provide an alternative solution to optically interacting with the sample 310 in applications where the sample 310 may be difficult to access or is otherwise out of a direct line of sight for the detection end 308a of the analyzer 300. For instance, the fiber optic probes 328 may be advanced into cavities and tubular structures, thereby providing an easier way of accessing and analyzing chemical compositions found within storage vessels, tanks, or other such sealed containers which make it difficult to transmit or receive electromagnetic radiation directly from the detection end 308a of the analyzer 300. The fiber optic probes 328 may be especially advantageous and convenient in applications where the sample 310 is, for example, engine/machine lubricant, coolant, hydraulic fluid, or fuels that are stored or otherwise contained in enclosed vessels. While the body 304 of the handheld characteristic analyzer 300 may not be able to access the interior of such enclosed vessels, the fiber optic probes 328 may be configured to penetrate such enclosed vessels through designated access ports defined therein. Accordingly, the fiber optic probes 328 essentially deliver the handheld characteristic analyzer 300 to hard-to-reach samples 310.

In some embodiments, the analyzer 300 may further include a battery 328 or other power source used to provide power to the various internal components of the analyzer 300. As depicted, the battery 328 may be communicably coupled to at least each of the optical computing device 312, the signal processor 314, and the GUI 324. The battery 328 may be rechargeable or otherwise replaceable, depending on the application or design considerations for the analyzer 300. Those skilled in the art, however, will readily recognize that many alternative means are available to power the analyzer 300, without departing from the scope of the present disclosure.

Those skilled in the art will further readily appreciate the various and numerous applications that the handheld characteristic analyzer 300, and its alternative configurations, may be suitably used with. For example, the sample 310 may be a machinery lubricant, grease, hydraulic fluid, or coolant fluid, and the analyzer 300 may be useful in detecting contaminants in the sample 310 such as, but not limited to water, soot, glycol, oxidation products, wear debris, particulate contamination, barium, calcium, magnesium, phosphorus, zinc, iron, copper, lead, combinations thereof, or the like. The analyzer 300 may also be useful in detecting physical properties of the sample 310 such as, but not limited to, pH, total dissolved solids, opacity, density/specific gravity, and viscosity.

In other embodiments, the sample 310 may be drinking water, and the analyzer 300 may be useful in detecting hazardous substances in the sample 310 such as, but not limited to, aluminum, chloride, copper, mercury, lead, arsenic, fluoride, iron, manganese, sulfate, zinc, disinefectants, inorganic chemicals, combinations thereof, and the like. In yet other embodiments, the sample 310 may be gasoline or diesel fuel, hydrocarbons in general, various treatment chemicals or solutions, and the analyzer 300 may be useful in detecting the concentration of, for example, water within the sample 310.

In yet other embodiments, the sample 310 may be a gas, such as a gaseous leak or other gaseous emission from a containment vessel or pipeline. For example, the sample 310 may refer to one or more hydrocarbon gases leaking from a pipeline, as well as one or more non-toxic tracers and/or gases such as nitrogen, carbon dioxide, and helium. The analyzer 300 may be useful in determining a characteristic of the sample 310, such as providing imaging of a specific chemical composition contained within the sample 310. In one application, the analyzer 300 may be directed to a weld or weldment on a pipeline or other fitting, and the GUI 324 may be configured to provide the user with a reading of, for example, any methane gas leaking around or from the weld. Accordingly, in real-time or near real-time, the user may be provided with a map of the chemical compound of interest. As can be appreciated, this could be applied to emissions monitoring and/or leak detection in any number of industries. This could also be applied in general pipeline inspection applications, where it is desired to determine whether any welds or connection points found along the length of a pipeline are properly sealed.

In some embodiments, the sample 310 may be separated production water after having undergone a water/oil separation process in conjunction with offshore hydrocarbon processing. It is often desirable to discharge the separated production water directly into the surrounding ocean, thereby eliminating the expense of pumping the fluid back downhole. Before the production water can be discharged into the ocean, however, it must first be rigorously tested to make sure that it does not contain any oil or other impurities that could damage the surrounding sea life. Accordingly, the analyzer 300 may be useful in determining a characteristic of interest of the sample 310, which may correspond to an impurity content of the production water, such as the presence of hydrocarbons, salts, bacteria, precipitates, particles, tags (e.g., chemical or physical), metals, organic compounds and volatile organic compounds, additives and treatments, polymers, bacteria, viruses, microorganisms, poisons, or other components of interest.

In other embodiments, the sample 310 may be acquired and then subsequently placed near, onto, or into the analyzer 300. For instance, the sample 310 could be acquired on/in a sample substrate or container, such as a paper strip, a microscope slide or the like, a pipette, a test tube, combinations thereof, and the like. Such embodiment, for example, may function somewhat similarly as a blood glucose meter, where the sample 310 may be physically introduced to the analyzer 300 on a single use strip, but in a configuration or arrangement that allows optical access to the sample 310 for monitoring and detection.

In yet other embodiments, the handheld chemical analyzer 300 may be used to monitor or otherwise analyze the substances or chemical compounds found on inline inspection devices, commonly called "pigs." For instance, pigs that have been retrieved from a pipeline, typically a gas line, can often be covered in substances or chemical compounds commonly referred to as "black dust." The analyzer 300 may be useful in analyzing the contents of the accumulated black dust, which could be toxic, radioactive, or otherwise hazardous. In operation, the analyzer 300 may be used to determine if the black dust is either harmless or hazardous, or to verify that the pig has been properly cleaned after retrieval and cleaning.

Figure 4:
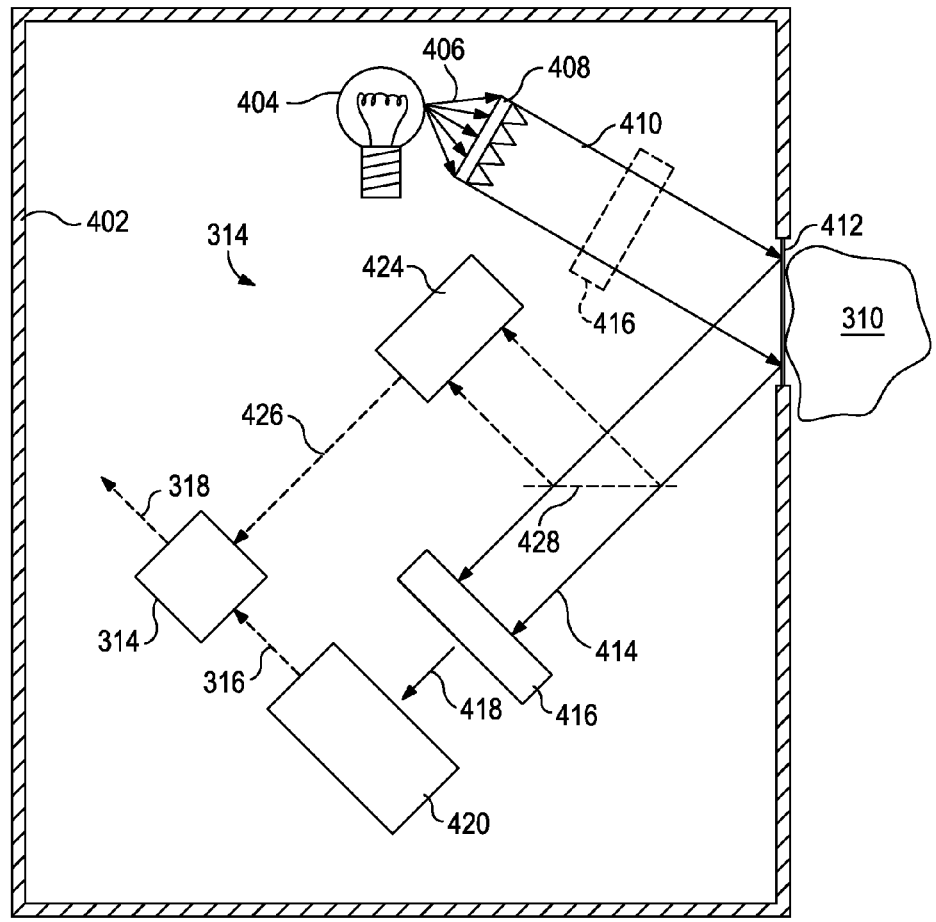
FIG. 4 illustrates an exemplary optical computing device able to monitor a sample chemical composition and determine a characteristic thereof, according to one or more embodiments.

Referring now to FIG. 4, with continued reference to FIG. 3, illustrated is an exemplary schematic view of the optical computing device 312, according to one or more embodiments. As briefly discussed above, in operation, the optical computing device 312 may be configured to determine a particular characteristic of interest in the sample 310, such as a concentration of a hazardous substance or contaminant that may be present within the sample 310. Knowing the concentration of known hazardous substances or contaminants may help determine the overall quality or health of the sample 310 and otherwise indicate a need to remedy potentially undesirable levels of hazardous substances.

As illustrated, the optical computing device 312 may be housed within a casing or housing 402. In at least one embodiment, the housing 402 may be same as the housing 304 of the handheld characteristic analyzer 300 of FIG. 3. In other embodiments, however, the housing 402 may be distinct from the housing 304 and otherwise configured to substantially protect the internal components of the device 312 from damage or contamination from the sample 310 or other external contaminants. In such embodiments, the housing 402 may operate to mechanically couple the device 312 to the handheld characteristic analyzer 300 with, for example, mechanical fasteners, brazing or welding techniques, adhesives, magnets, combinations thereof, or the like.

In one or more embodiments, the device 312 may include an electromagnetic radiation source 404 configured to emit or otherwise generate electromagnetic radiation 406. The electromagnetic radiation source 404 may be any device capable of emitting or generating electromagnetic radiation, as defined herein. For example, the electromagnetic radiation source 404 may be a light bulb, a light emitting device (LED), a laser, a blackbody, a photonic crystal, an X-Ray source, combinations thereof, or the like. In some embodiments, a lens 408 may be configured to collect or otherwise receive the electromagnetic radiation 406 and direct a beam 410 of electromagnetic radiation 406 toward a location for detecting the sample 310. The lens 408 may be any type of optical device configured to transmit or otherwise convey the electromagnetic radiation 406 as desired. For example, the lens 408 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 408 may be omitted from the device 312 and the electromagnetic radiation 406 may instead be directed toward the sample 310 directly from the electromagnetic radiation source 404.

In one or more embodiments, the device 312 may also include a sampling window 412. In at least one embodiment, the sampling window 412 may form part of the housing 304 of the handheld characteristic analyzer 300 of FIG. 3 and thereby provide a transmission location for the beam 410 of electromagnetic radiation 406 to optically interact with the sample 310. The sampling window 412 may be made from a variety of transparent, rigid or semi-rigid materials that are configured to allow transmission of the electromagnetic radiation 406 therethrough. For example, the sampling window 412 may be made of, but is not limited to, glasses, plastics, semi-conductors, crystalline materials, polycrystalline materials, hot or cold-pressed powders, combinations thereof, or the like. In order to remove ghosting or other imaging issues resulting from reflectance on the sampling window 412, the system 300 may employ one or more internal reflectance elements (IRE), such as those described in co-owned U.S. Pat. No. 7,697,141, and/or one or more imaging systems, such as those described in co-owned U.S. patent application Ser. No. 13/456,467, the contents of each hereby being incorporated by reference.

After passing through the sampling window 412, the electromagnetic radiation 406 impinges upon and optically interacts with the sample 310, including any hazardous substances or contaminants present therein. As a result, optically interacted radiation 414 is generated by and reflected from the sample 310. Those skilled in the art, however, will readily recognize that alternative variations of the device 312 may allow the optically interacted radiation 414 to be generated by being transmitted, scattered, diffracted, absorbed, emitted, or re-radiated by and/or from the sample 310, or one or more hazardous substances present within the sample 310, without departing from the scope of the disclosure.

The optically interacted radiation 414 generated by the interaction with the sample 310, and at least one hazardous substance present therein, may be directed to or otherwise be received by an ICE 416 arranged within the device 312. The ICE 416 may be a spectral component substantially similar to the ICE 100 described above with reference to FIG. 1. Accordingly, in operation the ICE 416 may be configured to receive the optically interacted radiation 414 and produce modified electromagnetic radiation 418 corresponding to a particular characteristic of interest of the sample 310. In particular, the modified electromagnetic radiation 418 is electromagnetic radiation that has optically interacted with the ICE 416, whereby an approximate mimicking of the regression vector corresponding to the characteristic of interest in the sample 310 is obtained. In one or more embodiments, the characteristic of interest corresponds to a concentration of the hazardous substance or contaminant present within the sample 310.

It should be noted that, while FIG. 4 depicts the ICE 416 as receiving reflected electromagnetic radiation from the sample 310, the ICE 416 may be arranged at any point along the optical train of the device 312, without departing from the scope of the disclosure. For example, in one or more embodiments, the ICE 416 (as shown in dashed) may be arranged within the optical train prior to the sampling window 412 and equally obtain substantially the same results. In other embodiments, the sampling window 412 may serve a dual purpose as both a transmission window and the ICE 416 (i.e., a spectral component). In yet other embodiments, the ICE 416 may generate the modified electromagnetic radiation 418 through reflection, instead of transmission therethrough.

Moreover, while only one ICE 416 is shown in the device 312, embodiments are contemplated herein which include the use of two or more ICE components in the device 312, each being configured to cooperatively determine the characteristic of interest in the sample 310. For example, two or more ICE components may be arranged in series or parallel within the device 312 and configured to receive the optically interacted radiation 414 and thereby enhance sensitivities and detector limits of the device 312. In other embodiments, two or more ICE components may be arranged on a movable assembly, such as a rotating disc or an oscillating linear array, which moves such that the individual ICE components are able to be exposed to or otherwise optically interact with electromagnetic radiation for a distinct brief period of time. The two or more ICE components in any of these embodiments may be configured to be either associated or disassociated with the characteristic of interest of the sample 310. In other embodiments, the two or more ICE components may be configured to be positively or negatively correlated with the characteristic of interest of the sample. These optional embodiments employing two or more ICE components are further described in co-pending U.S. patent application Ser. Nos. 13/456,264, 13/456,405, 13/456,302, and 13/456,327, the contents of which are hereby incorporated by reference in their entireties.

In some embodiments, it may be desirable to monitor more than one characteristic of interest at a time using the device 312. In such embodiments, various configurations for multiple ICE components can be used, where each ICE component is configured to detect a particular and/or distinct characteristic of interest. In some embodiments, the characteristic of interest can be analyzed sequentially using the multiple ICE components that are provided a single beam of electromagnetic radiation being reflected from or transmitted through the sample 310. In some embodiments, as briefly mentioned above, multiple ICE components can be arranged on a rotating disc, where the individual ICE components are only exposed to the beam of electromagnetic radiation for a short time. Advantages of this approach can include the ability to analyze multiple hazardous substances and contaminants within the sample 310 using a single optical computing device and the opportunity to assay additional hazardous substances simply by adding additional ICE components to the rotating disc.

In other embodiments, multiple optical computing devices 312 can be used at a single location (or at least on close proximity) within the sample 310, where each optical computing device 312 contains a unique ICE component that is configured to detect a particular characteristic of interest present in the sample 310, such as a particular hazardous substance or contaminant. Each optical computing device 312 can be coupled to a corresponding detector or detector array that is configured to detect and analyze an output of electromagnetic radiation from the respective optical computing device 312. Parallel configurations of optical computing devices 312 can be particularly beneficial for applications that require low power inputs and/or no moving parts.

The modified electromagnetic radiation 418 generated by the ICE 416 may subsequently be conveyed to a detector 420 for quantification of the signal. The detector 420 may be any device capable of detecting electromagnetic radiation, and may be generally characterized as an optical transducer. In some embodiments, the detector 420 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 420 may be configured to produce the output signal 316 (refer to FIG. 3A) in real-time or near real-time in the form of a voltage (or current) that corresponds to the particular characteristic of interest in the sample 310. The voltage returned by the detector 420 is essentially the dot product of the optical interaction of the optically interacted radiation 414 with the respective ICE 416 as a function of the concentration of the characteristic of interest of the sample 310. As such, the output signal 316 produced by the detector 420 and the concentration of the characteristic of interest in the sample 310 may be related, for example, directly proportional. In other embodiments, however, the relationship may correspond to a polynomial function, an exponential function, a logarithmic function, and/or a combination thereof.

In some embodiments, the device 312 may include a second detector 424, which may be similar to the first detector 420 in that it may be any device capable of detecting electromagnetic radiation. Similar to the second detector 216 of FIG. 2, the second detector 424 of FIG. 4 may be used to detect radiating deviations stemming from the electromagnetic radiation source 404. Undesirable radiating deviations can occur in the intensity of the electromagnetic radiation 406 due to a wide variety of reasons and potentially causing various negative effects on the device 312. These negative effects can be particularly detrimental for measurements taken over a period of time. In some embodiments, radiating deviations can occur as a result of a build-up of film or material on the sampling window 412 which has the effect of reducing the amount and quality of light ultimately reaching the first detector 420. Without proper compensation, such radiating deviations could result in false readings and the output signal 316 would no longer be primarily or accurately related to the characteristic of interest.

To compensate for these types of undesirable effects, the second detector 424 may be configured to generate a compensating signal 426 generally indicative of the radiating deviations of the electromagnetic radiation source 404, and thereby normalize the output signal 316 generated by the first detector 420. As illustrated, the second detector 424 may be configured to receive a portion of the optically interacted radiation 414 via a beamsplitter 428 in order to detect the radiating deviations. In other embodiments, however, the second detector 424 may be arranged to receive electromagnetic radiation from any portion of the optical train in the device 312 in order to detect the radiating deviations, without departing from the scope of the disclosure.

As illustrated, the output signal 316 and the compensating signal 426 may be conveyed to or otherwise received by the signal processor 314 (refer to FIG. 3A) communicably coupled to both the detectors 420, 424. In one or more embodiments, the signal processor 314 may be a computer including a non-transitory machine-readable medium, and may be configured to computationally combine the compensating signal 426 with the output signal 316 in order to normalize the output signal 316 in view of any radiating deviations detected by the second detector 424. In some embodiments, computationally combining the output and compensating signals 316, 426 may entail computing a ratio of the two signals 316, 426. For example, the concentration or magnitude of each characteristic of interest determined using the optical computing device 312 can be fed into an algorithm run by the signal processor 314. The algorithm may be configured to make predictions on how the characteristics of the sample 310 change if the concentration of the measured characteristic of interest changes.

In real-time or near real-time, the signal processor 314 may be configured to provide the resulting output signal 318 (refer to FIG. 3A) corresponding to the characteristic of interest, such as the concentration of the hazardous substance present in the sample 310. As briefly discussed above, the resulting signal output signal 318 may be conveyed, either wired or wirelessly, to an operator for analysis and consideration. In other embodiments, the resulting output signal 318 may be conveyed to a GUI 324 (FIG. 3A) which may be configured to provide a graphical representation of the characteristic of interest for consideration by of the user. Upon review of the resulting output signal 318, the operator may be able to determine which hazardous substances are present in the sample 310, and in what concentration.

Figure 5:
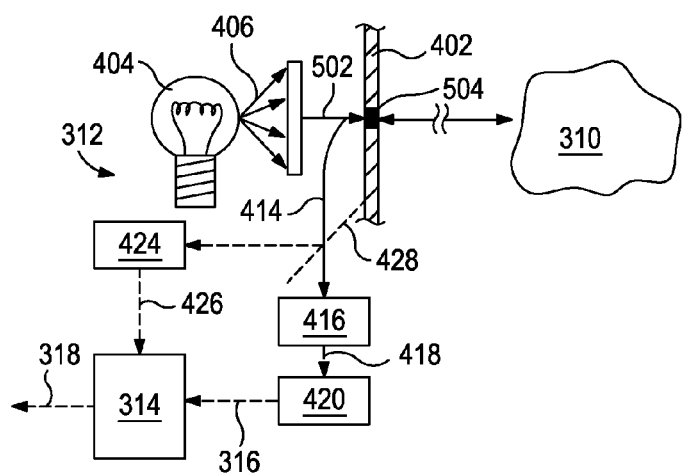
FIG. 5 illustrates another exemplary optical computing device able to monitor a sample chemical composition and determine a characteristic thereof, according to one or more embodiments.

Referring now to FIG. 5, with continued reference to FIG. 4, illustrated is an alternative embodiment of the optical computing device 312, according to one or more embodiments. The optical computing device 312 of FIG. 5 includes one or more fiber optic probes 502 used to optically interact with the sample 310. The fiber optic probes 502 may be similar to the fiber optic probes 328 of FIG. 3A, and therefore will not be described again in detail. As illustrated, the electromagnetic radiation 406 may be fed into or otherwise provided to the fiber optic probes 502 which may be configured to convey the electromagnetic radiation 406 to the sample 310. Specifically, the fiber optic probes 502 may be configured to penetrate the housing 402 at a connection hub 504 defined in the housing 402. In at least one embodiment, the connection hub 504 may provide a location in the housing 402 where the fiber optic probe 502 may be releasably attached to the device 312.

After the electromagnetic radiation 406 has optically interacted with the sample 310, the fiber optic probes 502 may also be configured to return optically interacted radiation 414 back to the device 312 and convey the same to the ICE 416. The ICE 416, in turn, receives the optically interacted radiation 414 and produces the modified electromagnetic radiation 418 corresponding to the particular characteristic of interest of the sample 310, such as a concentration of a hazardous substance or contaminant found therein. It should be noted that, while FIG. 5 depicts the ICE 416 as receiving electromagnetic radiation from the sample 310 via the fiber optic probe 502, the ICE 416 may be arranged at any point along the optical train of the device 312, without departing from the scope of the disclosure. For example, in one or more embodiments, the ICE 416 may equally be arranged within the optical train prior to the connection hub 504, and equally obtain substantially the same results.

As generally described above with reference to FIG. 4, the modified electromagnetic radiation 418 generated by the ICE 416 may subsequently be conveyed to the detector 420 for quantification of the signal. In real-time or near real-time, the detector 420 may produce the output signal 316 in the for of a voltage (or current) that corresponds to the particular characteristic of interest in the sample 310. The second detector 424 may detect radiating deviations stemming from the electromagnetic radiation source 404, and subsequently generate the compensating signal 426. The output signal 316 and the compensating signal 426 may then be conveyed to or otherwise received by the signal processor 314 which computationally combines the signals 316, 426 in order to normalize the output signal 316. Lastly, the resulting output signal 318 corresponding to the characteristic of interest (e.g., the concentration of the hazardous substance present in the sample 310), may be conveyed, either wired or wirelessly, to an operator for analysis and consideration. In other embodiments, the resulting output signal 318 may be conveyed to a GUI 324 (FIG. 3A) which may be configured to provide a graphical representation of the characteristic of interest for consideration by of the user. Upon review of the resulting output signal 318, the operator may be able to determine which hazardous substances are present in the sample 310, and in what concentration.

Referring to both FIGS. 4 and 5, those skilled in the art will readily recognize that, in one or more embodiments, electromagnetic radiation may be derived from the sample 310 itself or the ambient environment in which the sample 310 resides, and otherwise derived independent of the electromagnetic radiation source 404. For example, various substances naturally radiate electromagnetic radiation that is able to optically interact with the ICE 416. In some embodiments, for example, the sample 310 or a substance within the sample 310 may be a blackbody radiating substance configured to radiate heat that may optically interact with the ICE 416. In other embodiments, the sample 310 or the substance within the sample 310 may be radioactive or chemo-luminescent and, therefore, radiate electromagnetic radiation that is able to optically interact with the ICE 416. In yet other embodiments, the electromagnetic radiation may be induced from the sample 310 or the hazardous substance within the sample 310 by being acted upon mechanically, magnetically, electrically, combinations thereof, or the like. For instance, in at least one embodiment, a voltage may be applied to the sample 310 in order to induce the electromagnetic radiation. In yet other embodiments, the electromagnetic radiation may be provided from ambient light (e.g., sunlight, artificial light, etc.). As a result, embodiments are contemplated herein where the electromagnetic radiation source 404 is omitted from the particular optical computing device.

Those skilled in the art will readily appreciate that the optical computing device 312, and its components described herein, are not necessarily drawn to scale nor, strictly speaking, depicted as optically correct as understood by those skilled in optics. Instead, FIGS. 4 and 5 are merely illustrative in nature and used generally herein in order to supplement understanding of the description of the various exemplary embodiments. Nonetheless, while FIGS. 4 and 5 may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A handheld characteristic analyzer, comprising:
a portable housing;
at least one optical computing device arranged within the portable housing for monitoring a sample, the at least one optical computing device having at least one integrated computational element configured to optically interact with the sample and thereby generate optically interacted light;
at least one detector arranged to receive the optically interacted light and generate an output signal corresponding to a characteristic of the sample; and
a signal processor communicably coupled to the at least one detector for receiving the output signal, the signal processor being configured to determine the characteristic of the sample and provide a resulting output signal indicative of the characteristic of the sample, wherein the integrated computational element comprises a plurality of alternating layers of two materials, each of the plurality of alternating layers of two materials having a thickness selected to form an amplitude of the optically interacted light proportional to a vector product of a loaded regression vector and an input light beam.

2. The handheld characteristic analyzer of claim 1, further comprising a handle extending from the portable housing and providing a location for holding the handheld characteristic analyzer.

3. The handheld characteristic analyzer of claim 2, further comprising a trigger mechanism defined on the portable housing and engageable to activate the handheld characteristic analyzer.

4. The handheld characteristic analyzer of claim 1, wherein the characteristic of the sample is a concentration of a substance present within the sample.

5. The handheld characteristic analyzer of claim 1, wherein the sample is a fluid.

6. The handheld characteristic analyzer of claim 5, wherein the fluid comprises at least one selected from the group consisting of drinking water, separated production water, gasoline fuel, diesel fuel, a gas, machinery lubricant, grease, hydraulic fluid, coolant fluid, and any combinations thereof.

7. The handheld characteristic analyzer of claim 1, wherein the sample is a solid substance.

8. The handheld characteristic analyzer of claim 1, further comprising a communication port defined on the portable housing and communicably coupled to the signal processor, the signal processor being configured to convey the resulting output signal to the communication port.

9. The handheld characteristic analyzer of claim 1, further comprising a wireless link arranged within the portable housing and communicably coupled to the signal processor, the signal processor being configured to convey the resulting output signal to the wireless link.

10. The handheld characteristic analyzer of claim 1, further comprising a graphical user interface arranged on the portable housing and communicably coupled to the signal processor, the signal processor being configured to convey the resulting output signal to the graphical user interface.

11. The handheld characteristic analyzer of claim 10, wherein the graphical user interface is configured to provide one or more visual representations of the characteristic of the sample.

12. The handheld characteristic analyzer of claim 11, wherein the one or more visual representations of the characteristic of the sample includes an optical spectra of the characteristic of the sample.

13. The handheld characteristic analyzer of claim 10, wherein the graphical user interface is configured to display a visual light image.

14. The handheld characteristic analyzer of claim 13, wherein the graphical user interface provides one or more visual representations of the characteristic of the sample, and wherein the visual light image is overlaid with the one or more visual representations.

15. The handheld characteristic analyzer of claim 1, further comprising one or more fiber optic probes communicably coupled to the at least one optical computing device and configured convey optically interacted radiation from the sample to the optical computing device.

16. The handheld characteristic analyzer of claim 15, wherein the at least one optical computing device further comprises an electromagnetic radiation source configured to emit electromagnetic radiation, the one or more fiber optic probes being configured to convey the electromagnetic radiation to the sample.

17. The handheld characteristic analyzer of claim 15, wherein the one or more fiber optic probes are detachably coupled to the portable housing.

18. The handheld characteristic analyzer of claim 1, wherein the at least one optical computing device further comprises an electromagnetic radiation source configured to emit electromagnetic radiation that optically interacts with the sample, and wherein the at least one detector is a first detector and the system further comprises a second detector arranged to detect the electromagnetic radiation from the electromagnetic radiation source and thereby generate a compensating signal indicative of electromagnetic radiating deviations.

19. The handheld characteristic analyzer of claim 18, wherein the signal processor is communicably coupled to the first and second detectors and configured to receive and computationally combine the output and compensating signals in order to normalize the output signal and determine the characteristic of the sample.

* * * * *